(12) United States Patent
Yeung et al.

(10) Patent No.: US 11,399,936 B2
(45) Date of Patent: *Aug. 2, 2022

(54) TRANSCATHETER PROSTHETIC HEART VALVE POST-DILATATION REMODELING DEVICES AND METHODS

(71) Applicant: Medtronic, Inc., Minneapolis, MN (US)

(72) Inventors: Hubert Yeung, Santa Rosa, CA (US); Mike Krivoruchko, Forestville, CA (US); Susheel Deshmukh, Santa Rosa, CA (US)

(73) Assignee: Medtronic, Inc., Minneapolis, MN (US)

( * ) Notice: Subject to any disclaimer, the term of this patent is extended or adjusted under 35 U.S.C. 154(b) by 301 days.

This patent is subject to a terminal disclaimer.

(21) Appl. No.: 16/593,088

(22) Filed: Oct. 4, 2019

(65) Prior Publication Data

US 2020/0030094 A1 Jan. 30, 2020

Related U.S. Application Data

(60) Continuation of application No. 15/252,279, filed on Aug. 31, 2016, now Pat. No. 10,449,045, which is a (Continued)

(51) Int. Cl.
*A61F 2/24* (2006.01)
*A61M 25/10* (2013.01)
*A61F 2/95* (2013.01)

(52) U.S. Cl.
CPC .......... *A61F 2/2433* (2013.01); *A61F 2/2418* (2013.01); *A61F 2/2436* (2013.01); (Continued)

(58) Field of Classification Search
CPC .. A61F 2/95; A61F 2/958; A61F 2/962; A61F 2/966; A61F 2/2427; A61F 2/243; (Continued)

(56) References Cited

U.S. PATENT DOCUMENTS 5,522,882 A 6/1996 Gaterud et al.
5,683,451 A 11/1997 Lenker et al.
(Continued)

FOREIGN PATENT DOCUMENTS

GB 2433700 7/2007
WO 08/138584 11/2008
WO 09/091509 7/2009

*Primary Examiner* — George J Ulsh
(74) *Attorney, Agent, or Firm* — Dicke, Billig & Czaja, PLLC

(57) ABSTRACT

A system and method for restoring (e.g., replacing) a defective heart valve of a patient. A delivery system is manipulated to percutaneously deliver and implant a stented prosthetic heart valve to a native heart valve. A post-dilatation balloon is percutaneously delivered to the implantation site, and a compliant segment thereof is arranged within a region of the implanted prosthesis. The balloon is inflated such that the compliant segment expands and contacts the prosthesis, expanding a remodeling region of the prosthesis to a remodeled state. With these and related techniques, remodeling of an implanted, stented prosthetic heart valve to better match the native valve shape is possible, providing many benefits such as reducing the risk of paravalvular leaks.

10 Claims, 16 Drawing Sheets

Related U.S. Application Data continuation of application No. 14/031,330, filed on Sep. 19, 2013, now Pat. No. 9,456,899, which is a division of application No. 13/094,455, filed on Apr. 26, 2011, now Pat. No. 8,568,474.

(60) Provisional application No. 61/328,068, filed on Apr. 26, 2010.

(52) U.S. Cl.
CPC ........... *A61F 2/95* (2013.01); *A61M 25/1002* (2013.01); *A61F 2002/9534* (2013.01); *A61F 2230/008* (2013.01); *A61F 2230/0054* (2013.01); *A61F 2250/0018* (2013.01); *A61F 2250/0039* (2013.01); *A61M 25/104* (2013.01); *A61M 2025/1059* (2013.01)

(58) Field of Classification Search
CPC ........ A61F 2/2433; A61F 2/2436; A61F 2/24; A61F 2/2418; A61F 2250/018; A61F 2250/0039; A61F 6/146; A61F 6/20; A61M 25/1002; A61M 25/10; A61M 2025/1059; A61B 1/00082; A61B 5/6853; A61B 17/12022; A61B 17/0057
See application file for complete search history.

(56) References Cited

U.S. PATENT DOCUMENTS

| | | | |
|---|---|---|---|
| 5,824,041 | A | 10/1998 | Lenker et al. |
| 5,906,619 | A | 5/1999 | Olson et al. |
| 5,957,949 | A | 9/1999 | Leonhardt et al. |
| 6,027,486 | A | 2/2000 | Crocker |
| 6,409,741 | B1 | 6/2002 | Crocker et al. |
| 6,875,231 | B2 | 4/2005 | Anduiza et al. |
| 7,435,257 | B2 | 10/2008 | Lashinski et al. |
| 7,854,762 | B2 | 12/2010 | Speziali et al. |
| 2003/0199963 | A1 | 10/2003 | Tower et al. |
| 2004/0138731 | A1 | 7/2004 | Johnson |
| 2004/0210304 | A1 | 10/2004 | Seguin et al. |
| 2005/0090846 | A1 | 4/2005 | Pedersen et al. |
| 2005/0137688 | A1 | 6/2005 | Salahieh et al. |
| 2005/0137690 | A1 | 6/2005 | Salahieh et al. |
| 2006/0052867 | A1 | 3/2006 | Revuelta et al. |
| 2006/0135985 | A1 | 6/2006 | Cox et al. |
| 2006/0259136 | A1 | 11/2006 | Nguyen et al. |
| 2006/0265056 | A1 | 11/2006 | Nguyen et al. |
| 2007/0005131 | A1 | 1/2007 | Taylor |
| 2007/0088431 | A1 | 4/2007 | Bourang et al. |
| 2007/0203561 | A1 | 8/2007 | Forster et al. |
| 2007/0239266 | A1 | 10/2007 | Birdsall |
| 2007/0239269 | A1 | 10/2007 | Dolan et al. |
| 2008/0065011 | A1 | 3/2008 | Marchand et al. |
| 2008/0082165 | A1 | 4/2008 | Wilson et al. |
| 2008/0132989 | A1 | 6/2008 | Snow et al. |
| 2008/0147160 | A1 | 6/2008 | Ghione et al. |
| 2008/0147181 | A1 | 6/2008 | Ghione et al. |
| 2008/0188928 | A1 | 8/2008 | Salahieh et al. |
| 2008/0215144 | A1 | 9/2008 | Ryan et al. |
| 2009/0093876 | A1 | 4/2009 | Nitzan et al. |
| 2009/0138079 | A1 | 5/2009 | Tuval et al. |
| 2009/0171447 | A1 | 7/2009 | Von Segesser et al. |
| 2009/0177275 | A1 | 7/2009 | Case |
| 2009/0281619 | A1 | 11/2009 | Le et al. |
| 2010/0076548 | A1 | 3/2010 | Konno |
| 2010/0094411 | A1 | 4/2010 | Tuval et al. |
| 2010/0121434 | A1 | 5/2010 | Paul et al. |
| 2010/0131039 | A1 | 5/2010 | Chau et al. |
| 2010/0234940 | A1 | 9/2010 | Dolan |
| 2011/0144742 | A1 | 6/2011 | Madrid et al. |
| 2011/0251683 | A1 | 10/2011 | Tabor |
| 2011/0264198 | A1 | 10/2011 | Murray et al. |
| 2011/0264201 | A1 | 10/2011 | Yeung et al. |
| 2011/0301688 | A1 | 12/2011 | Dolan |
| 2012/0209375 | A1 | 8/2012 | Madrid et al. |

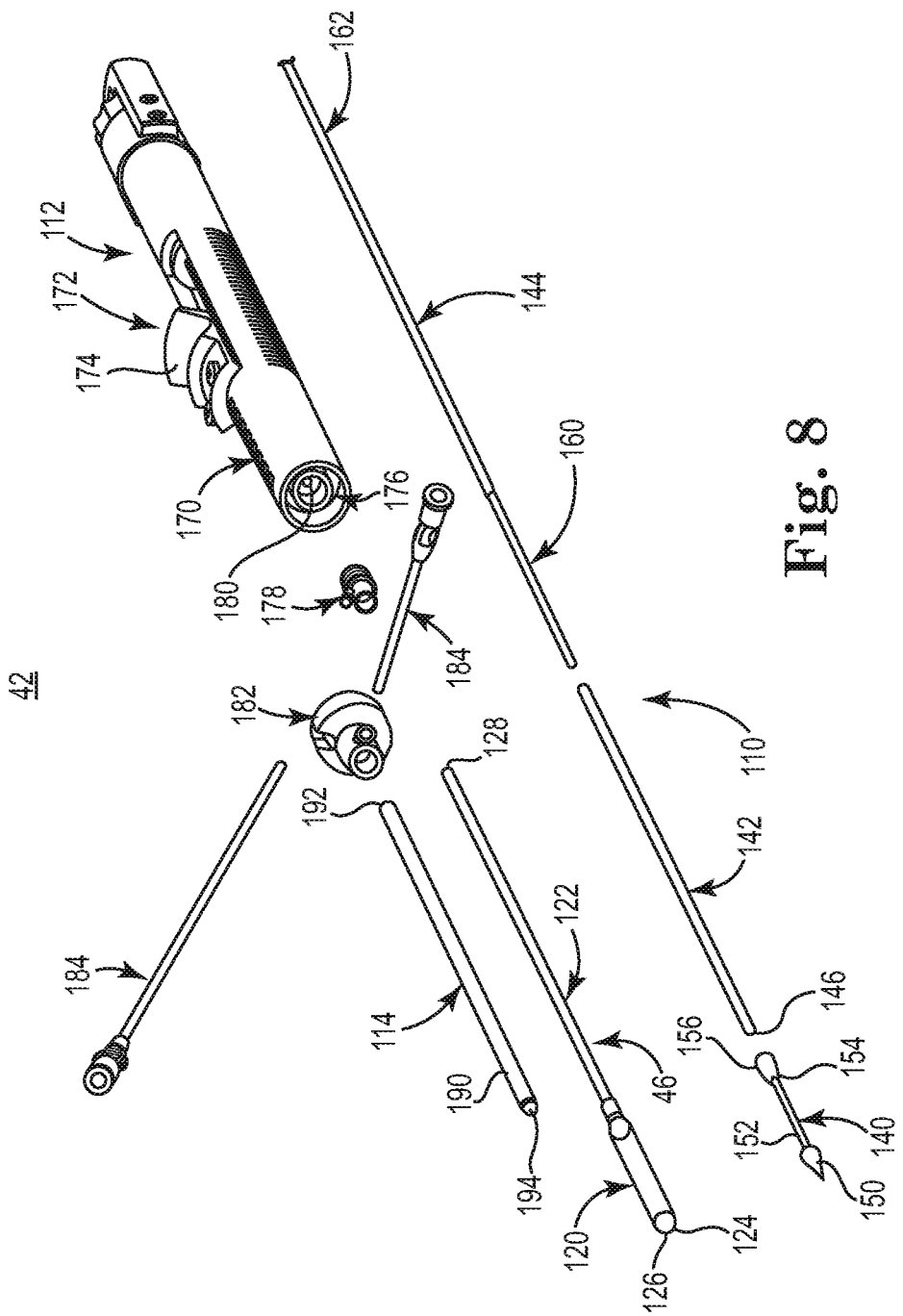

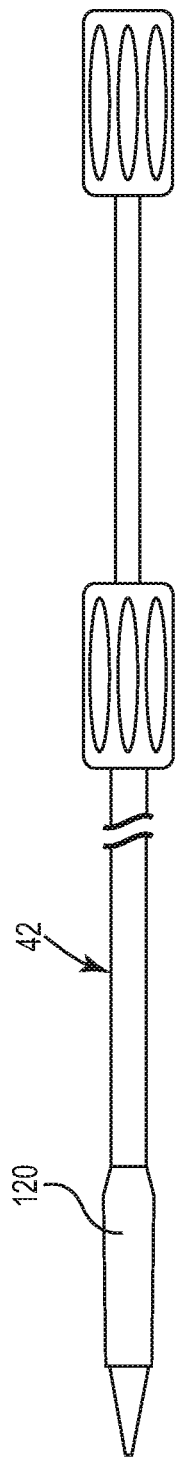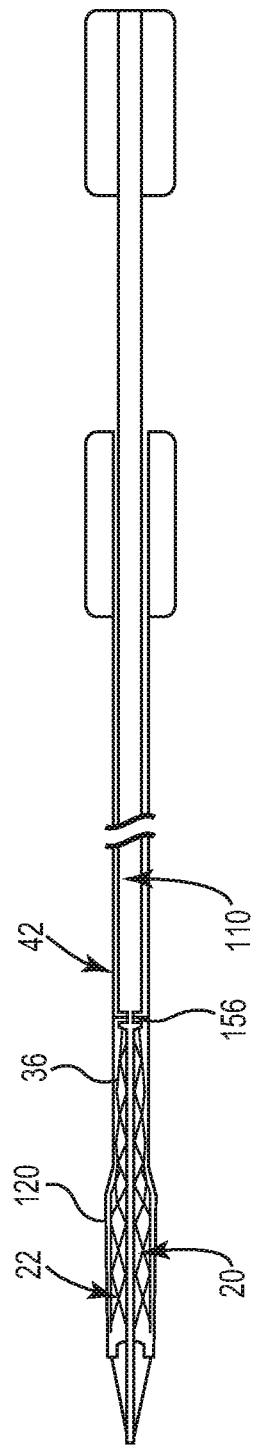

TRANSCATHETER PROSTHETIC HEART VALVE POST-DILATATION REMODELING DEVICES AND METHODS

CROSS-REFERENCE TO RELATED APPLICATIONS

This application is a Continuation of and claims priority to U.S. patent application Ser. No. 15/252,279, filed on Aug. 31, 2016, now allowed, which is a Continuation of and claims priority to U.S. patent application Ser. No. 14/031,330, filed on Sep. 19, 2013, now U.S. Pat. No. 9,456,899, which is a Division of and claims priority to U.S. patent application Ser. No. 13/094,455, filed on Apr. 26, 2011, now U.S. Pat. No. 8,568,474, which claims priority under 35 U.S.C. § 119(e)(1) to U.S. Provisional Patent Application Ser. No. 61/328,068, filed on Apr. 26, 2010, the entire teachings of which are incorporated herein by reference.

BACKGROUND

The present disclosure relates to systems, devices, and methods for percutaneous implantation of a prosthetic heart valve. More particularly, it relates to systems, devices, and methods for percutaneously remodeling an implanted stented prosthetic heart valve.

Diseased or otherwise deficient heart valves can be repaired or replaced with an implanted prosthetic heart valve. Conventionally, heart valve replacement surgery is an open-heart procedure conducted under general anesthesia, during which the heart is stopped and blood flow is controlled by a heart-lung bypass machine. Traditional open surgery inflicts significant patient trauma and discomfort, and exposes the patient to a number of potential risks, such as infection, stroke, renal failure, and adverse effects associated with the use of the heart-lung bypass machine, for example.

Due to the drawbacks of open-heart surgical procedures, there has been an increased interest in minimally invasive and percutaneous replacement of cardiac valves. With percutaneous transcatheter (or transluminal) techniques, a valve prosthesis is compacted for delivery in a catheter and then advanced, for example, through an opening in the femoral artery and through the descending aorta to the heart, where the prosthesis is then deployed in the annulus of the valve to be replaced (e.g., the aortic valve annulus). Although transcatheter techniques have attained widespread acceptance with respect to the delivery of conventional stents to restore vessel patency, only mixed results have been realized with percutaneous delivery of the more complex prosthetic heart valve.

Various types and configurations of prosthetic heart valves are available for percutaneous valve procedures, and continue to be refined. The actual shape and configuration of any particular transcatheter prosthetic heart valve is dependent to some extent upon the native shape and size of the valve being repaired (i.e., mitral valve, tricuspid valve, aortic valve, or pulmonary valve). In general, prosthetic heart valve designs attempt to replicate the functions of the valve being replaced and thus will include valve leaflet-like structures. With a bioprostheses construction, the replacement valve may include a valved vein segment that is mounted in some manner within an expandable stent frame to make a valved stent (or "stented prosthetic heart valve"). For many percutaneous delivery and implantation devices, the stent frame of the valved stent is made of a self-expanding material and construction. With these devices, the valved stent is crimped down to a desired size and held in that compressed arrangement within an outer sheath, for example. Retracting the sheath from the valved stent allows the stent to self-expand to a larger diameter, such as when the valved stent is in a desired position within a patient. In other percutaneous implantation systems, the valved stent can be initially provided in an expanded or uncrimped condition, then crimped or compressed on a balloon portion of a catheter until it is as close to the diameter of the catheter as possible. Once delivered to the implantation site, the balloon is inflated to deploy the prosthesis. With either of these types of percutaneous stented valve delivery devices, conventional sewing of the prosthetic heart valve to the patient's native tissue is typically not necessary.

With transcatheter delivery, it is imperative that the stented prosthetic heart valve be accurately located relative to the native annulus immediately prior to full deployment from the catheter as successful implantation requires the prosthetic heart valve to intimately lodge and seal against the native annulus. If the prosthesis is incorrectly positioned relative to the native annulus, serious complications can result such as leaks or even dislodgement from the native valve implantation site. Further, even if optimally located, problems may arise if the implanted prosthesis does not closely "fit" the native anatomy, including paravalvular leakage, migration due to hydrodynamic forces, and damage to surrounding tissues (e.g., aorta, cardiac tissue, etc.). As a point of reference, these same concerns do not normally arise in the context of conventional vascular stent implantation; with these procedures, the stent will perform its intended function regardless of whether the expanded shape closely matches the native anatomy.

In light of the above concerns, a clinician may employ imaging technology to evaluate the native heart valve anatomy prior to performing the implantation procedure, selecting an optimally sized prosthesis based on the evaluation. However, only the size of the selected prosthesis is affected by this evaluation, and not the overall shape. Thus, while the differently sized transcatheter prosthetic heart valves made available to the clinician are generally shaped in accordance with the expected native valve anatomy, it is unlikely that a selected prosthesis will actually "match" the actual native shape. Further, there are significant limitations associated with current imaging-based sizing procedures for transcatheter prosthetic heart valves. For example, measurements are currently only taken in one or two dimensional views and therefore may not account for annular ellipticity; identifying the true leaflet basal hinge point can be difficult with calcification, imaging errors, and the non-orthogonal geometry of a tricuspid valve; unknown annular compliance makes cross-sectional geometry of an implanted stent frame difficult to predict, which can lead to unacceptable stent aspect ratios and replacement valve performance; and variable calcification profiles may interact unpredictably with the stent frame. Unfortunately, conventional transcatheter prosthetic heart valve implantation devices do not readily permit in situ remodeling or shaping of a deployed heart valve prosthesis.

In light of the above, a need exists for transcatheter prosthetic heart valve delivery systems and methods that facilitate modeling of an implanted prosthesis to the native valve anatomy.

SUMMARY

Some aspects in accordance with principles of the present disclosure relate to a method of restoring (e.g., replacing) a defective heart valve of a patient. The method includes manipulating a delivery device to percutaneously deliver a stented prosthetic heart valve in a compressed arrangement to an implantation site of the defective heart valve. The stented prosthetic heart valve includes a stent frame to which a valve structure is attached, with the stent frame being configured to radially self-expand from the compressed arrangement. The delivery device is operated to release the stented prosthetic heart valve, including permitting the stent frame to self-expand from the compressed arrangement toward a deployed arrangement in which the prosthesis is implanted within the defective heart valve in an initial state. A post-dilatation balloon is percutaneously delivered, in a deflated state, to the implantation site. A compliant segment of the balloon is arranged within a region of the implanted stented prosthetic heart valve for which remodeling is desired. The balloon is then inflated such that the compliant segment expands and contacts the implanted stented prosthetic heart valve in the remodeling region. The remodeling region is expanded from the initial state via continued inflation of the compliant segment to alter a shape of the implanted prosthetic heart valve to a remodeled state. In some embodiments, the method includes directing the delivery device through a catheter to deliver the compressed prosthesis to the implantation site, followed by removal of the delivery device and subsequent insertion of the balloon through the catheter. In other embodiments, the implanted prosthetic heart valve defines an inflow side and an outflow side, with the compliant segment contacting the stent frame at a location between the inflow and outflow sides. In related embodiments, the balloon further includes first and second segments at immediately opposite sides of the compliant segment, respectively, with the first and second segments expanding to a predetermined maximum outer diameter while the compliant segment increases in maximum outer diameter with continued inflation of the balloon. With these and related techniques, remodeling of an implanted, stented prosthetic heart valve to better match the native shape is possible, providing many benefits such as reducing the risk of paravalvular leaks, optimal valve hydrodynamic performance, and durability.

Other aspects in accordance with principles of the present disclosure relate to a system for percutaneously restoring (e.g., replacing) a native heart valve of a patient. The system includes a stented prosthetic heart valve, a delivery device, and a post-dilatation balloon assembly. The stented prosthetic heart valve has a stent frame to which a valve structure is attached. The stent frame is configured to radially self-expand from a compressed arrangement. The delivery device includes a delivery sheath sized for percutaneously accessing a native heart valve. The delivery device provides a delivery state in which the delivery sheath compressively maintains the stented prosthetic heart valve in the compressed arrangement, as well as a deployment state in which the delivery sheath is withdrawn from the stented prosthetic heart valve to permit the prosthesis to self-expand from the compressed arrangement to a normal, expanded arrangement. The post-dilatation balloon assembly includes a catheter and a balloon fluidly attached to the catheter. The balloon is sized for percutaneously accessing the stented prosthetic heart valve once implanted to the native heart valve. In this regard, the balloon includes a compliant segment having a longitudinal length that is less than a longitudinal length of the prosthetic heart valve. Further, a maximum outer diameter of the compliant segment continuously expands with continuous inflation of the balloon. In some embodiments, the compliant segment has, in an inflated state of the balloon, an obround shape in longitudinal cross-section. In other embodiments, the balloon further defines first and second segments at immediately opposite sides of the compliant segment, respectively, with the first and second segments being less compliant than the compliant segment. In related embodiments, a wall thickness of the balloon along the compliant segment is less than a wall thickness of the balloon along the first and second segments.

BRIEF DESCRIPTION OF THE DRAWINGS

FIG. 8 is a perspective exploded view of a delivery device portion of the system of FIG. 2;

FIG. 9A is a simplified side view of the delivery device of FIG. 8 loaded with the prosthetic heart valve of FIG. 1B;

FIG. 9B is a simplified cross-sectional view of the loaded delivery device of FIG. 9A;

DETAILED DESCRIPTION

Figure 1A:
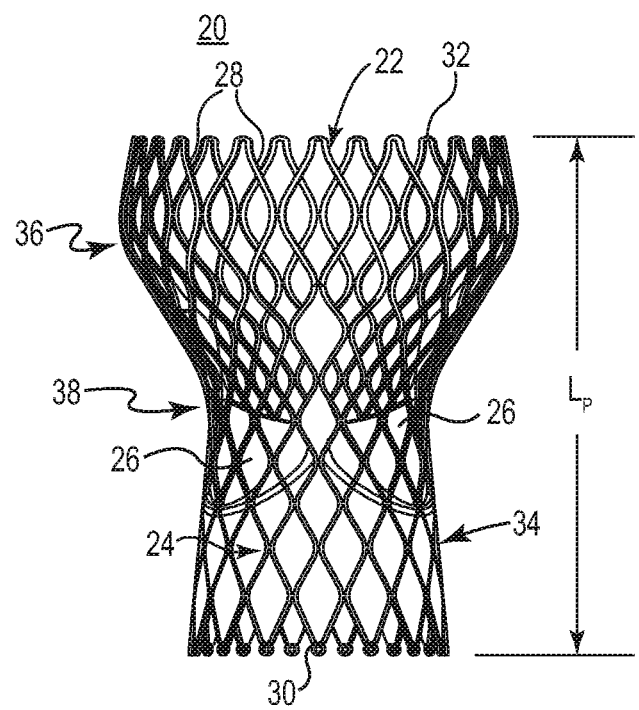
FIG. 1A is a side view of a stented prosthetic heart valve useful with systems, devices, and methods of the present disclosure and in a normal, expanded arrangement.

As referred to herein, stented transcatheter prosthetic heart valves useful with and/or as part of the various systems, devices, and methods of the present disclosure may assume a wide variety of different configurations, such as a bioprosthetic heart valve having tissue leaflets or a synthetic heart valve having a polymeric, metallic, or tissue-engineered leaflets, and can be specifically configured for replacing any heart valve. Thus, the stented prosthetic heart valve useful with the systems, devices, and methods of the present disclosure can be generally used for replacement of a native aortic, mitral, pulmonic, or tricuspid valves, for use as a venous valve, or to replace a failed bioprosthesis, such as in the area of an aortic valve or mitral valve, for example.

In general terms, the stented prosthetic heart valves of the present disclosure include a stent or stent frame maintaining a valve structure (tissue or synthetic), with the stent having a normal, expanded arrangement and collapsible to a compressed arrangement for loading within a delivery system. The stent is normally constructed to self-deploy or self-expand when released from the delivery system. For example, the stented prosthetic heart valve useful with the present disclosure can be a prosthetic valve sold under the trade name CoreValve® available from Medtronic CoreValve, LLC. Other non-limiting examples of transcatheter heart valve prostheses useful with systems, devices, and methods of the present disclosure are described in U.S. Publication Nos. 2006/0265056; 2007/0239266; and 2007/0239269, the teachings of each which are incorporated herein by reference. The stents or stent frames are support structures that comprise a number of struts or wire portions arranged relative to each other to provide a desired compressibility and strength to the prosthetic heart valve. In general terms, the stents or stent frames of the present disclosure are generally tubular support structures having an internal area in which valve structure leaflets will be secured. The leaflets can be formed from a variety of materials, such as autologous tissue, xenograph material, or synthetics as are known in the art. The leaflets may be provided as a homogenous, biological valve structure, such as porcine, bovine, or equine valves. Alternatively, the leaflets can be provided independent of one another (e.g., bovine or equine pericardial leaflets) and subsequently assembled to the support structure of the stent frame. In another alternative, the stent frame and leaflets can be fabricated at the same time, such as may be accomplished using high-strength nano-manufactured NiTi films produced at Advance BioProsthetic Surfaces (ABPS), for example. The stent frame support structures are generally configured to accommodate at least two (typically three) leaflets; however, replacement prosthetic heart valves of the types described herein can incorporate more or less than three leaflets.

Some embodiments of the stent frames can be a series of wires or wire segments arranged such that they are capable of self-transitioning from a compressed or collapsed arrangement to a normal, radially expanded arrangement. In some constructions, a number of individual wires comprising the stent frame support structure can be formed of a metal or other material. These wires are arranged in such a way that the stent frame support structure allows for folding or compressing or crimping to the compressed arrangement in which the internal diameter is smaller than the internal diameter when in the normal, expanded arrangement. In the compressed arrangement, such a stent frame support structure with attached valve leaflets can be mounted onto a delivery system. The stent frame support structures are configured so that they can be changed to their normal, expanded arrangement when desired, such as by the relative movement of one or more outer sheaths relative to a length of the stent frame.

The wires of these stent frame support structures in embodiments of the present disclosure can be formed from a shape memory and/or superelastic material such as a nickel titanium alloy (e.g., Nitinol™). With this material, the support structure is self-expandable from the compressed arrangement to the normal, expanded arrangement, such as by the application of heat, energy, and the like, or by the removal of external forces (e.g., radially compressive forces). This stent frame support structure can also be compressed and re-expanded multiple times without damaging the structure of the stent frame. In addition, the stent frame support structure of such an embodiment may be laser-cut from a single piece of material or may be assembled from a number of different components. For these types of stent frame structures, one example of a delivery device that can be used includes a catheter with a retractable sheath that covers the stent frame until it is to be deployed, at which point the sheath can be retracted to allow the stent frame to self-expand. Further details of such embodiments are discussed below.

Figure 1B:
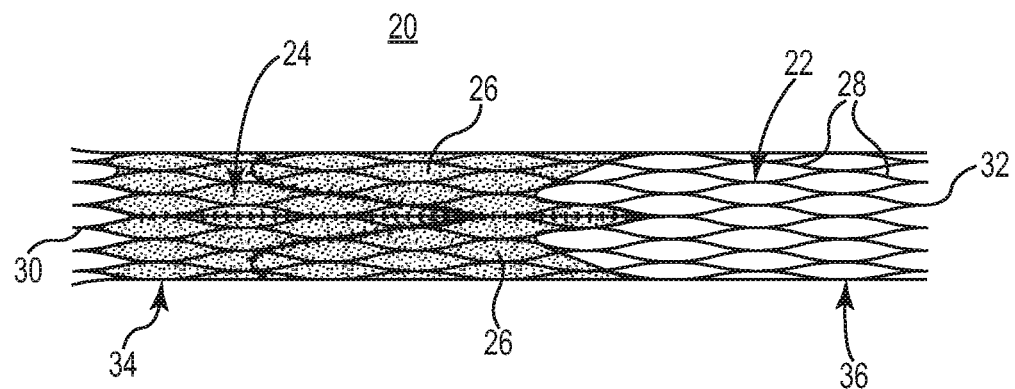
FIG. 1B is a side view of the prosthesis of FIG. 1A and in a compressed arrangement.

With the above understanding in mind, one non-limiting example of a stented prosthetic heart valve 20 useful with systems, devices, and methods of the present disclosure is illustrated in FIGS. 1A and 1B. As a point of reference, the prosthetic heart valve 20 is shown in a normal or expanded arrangement in the view of FIG. 1A; FIG. 1B illustrates the prosthetic heart valve 20 in a compressed arrangement (e.g., when compressively retained within an outer catheter or sheath). The prosthetic heart valve 20 includes a stent or stent frame 22 and a valve structure 24. The stent frame 22 can assume any of the forms described above, and is generally constructed so as to be self-expandable from the compressed arrangement (FIG. 1B) to the normal, expanded arrangement (FIG. 1A). In other embodiments, the stent frame 22 is expandable to the expanded arrangement by a separate device (e.g., a balloon internally located within the stent frame 22). The valve structure 24 is assembled to the stent frame 22 and provides two or more (typically three) leaflets 26. The valve structure 24 can assume any of the forms described above, and can be assembled to the stent frame 22 in various manners, such as by sewing the valve structure 24 to one or more of the wire segments 28 defined by the stent frame 22.

With the but one acceptable construction of FIGS. 1A and 1B, the prosthetic heart valve 20 is configured for restoring (e.g., replacing or repairing) an aortic valve. Alternatively, other shapes are also envisioned to adapt to the specific anatomy of the valve to be restored (e.g., stented prosthetic heart valves in accordance with the present disclosure can be shaped and/or sized for replacing a native mitral, pulmonic, or tricuspid valve). Regardless, the stent frame 22 defines an axial length $L_P$ of the prosthetic heart valve 20 as a longitudinal distance between opposing terminal ends 30, 32. With the one construction of FIGS. 1A and 1B, the valve structure 24 extends less than the entire length $L_P$ of the stent frame 22, but in other embodiments can extend along an entirety, or a near entirety, of the length $L_P$ of the stent frame 22. Regardless, an arrangement or orientation of the leaflets 26 establishes an inflow region 34 of the prosthetic heart valve 20, and an outflow region 36. As a point of reference, "inflow" and "outflow" terminology is in reference to an arrangement of the prosthetic heart valve 20 upon final implantation relative to the native aortic valve (or other valve) being replaced and the corresponding direction of blood flow therethrough. With these conventions, the first end 30 can serve as the inflow end of the prosthetic heart valve 20, and the second end 32 as the outflow end. Further, with the but one acceptable construction of FIG. 1A, a constriction region 38 can be formed at a transition from the inflow region 34 to the outflow region 36. A wide variety of constructions are also acceptable and within the scope of the present disclosure. For example, the stent frame 22 can have a more cylindrical shape in the normal, expanded arrangement.

Figure 2:
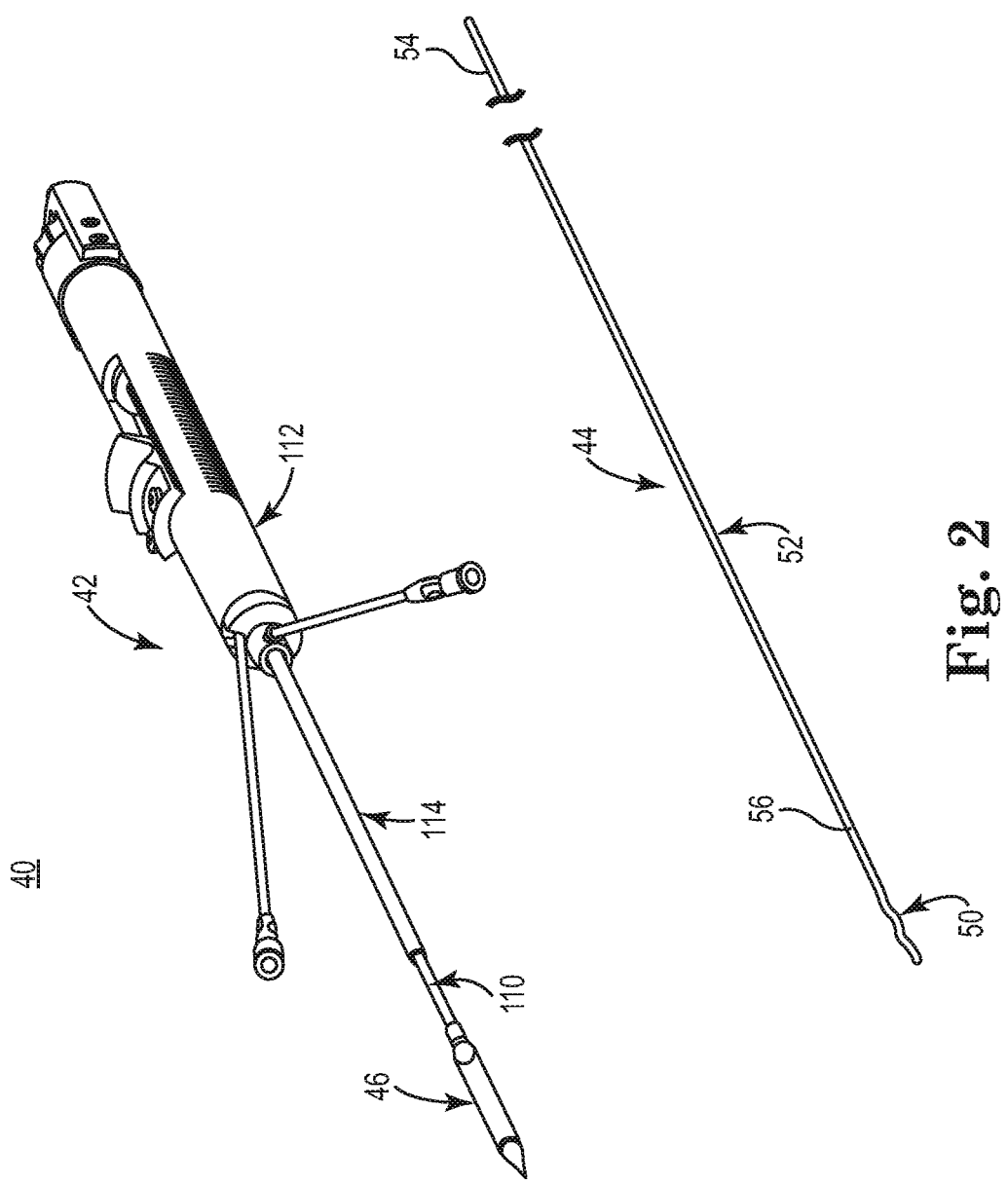
FIG. 2 is a perspective view of a system for restoring (e.g., replacing) a defective heart valve of a patient in accordance with principles of the present disclosure and with which the prosthesis of FIG. 1A is useful.

With the above understanding of the stented prosthetic heart valve 20 in mind, one embodiment of a system 40 in accordance with the present disclosure and useful in restoring (e.g., replacing) a defective heart valve is shown in FIG. 2. In addition to the prosthetic heart valve 20 (hidden in the view of FIG. 2), the system 40 includes a delivery device 42 and a post-dilatation assembly 44. Details on the various components are provided below. In general terms, however, the delivery device 42 is transitionable from a loaded state (shown in FIG. 2) in which the stented prosthetic heart valve 20 is contained within an outer delivery sheath 46 of the delivery device 42, to a deployed state in which the delivery sheath 46 is retracted from the prosthetic heart valve 20, thereby permitting the prosthetic heart valve 20 to self-expand (or alternatively be caused to expand by a separate mechanism) and release from the delivery device 42. Once released, the prosthesis 20 is implanted to the anatomy of the native valve being restored. Subsequently, a balloon 50 of the post-dilatation assembly 44 is percutaneously deployed and operated to remodel a region of the implanted prosthetic heart valve 20 as desired by the clinician. More generally, principles of the present disclosure are related to construction and/or implementation of the post-dilatation assembly 44 in remodeling an implanted prosthetic heart valve. The stented prosthetic heart valve 20 and the delivery device 42 can thus assume a plethora of different configurations directly or indirectly implicated by the descriptions provided herein.

The post-dilatation assembly 44 includes the balloon 50 and a catheter 52. The catheter 52 is coupled to the balloon 50 (or integrally forms the balloon 50), and fluidly connects the balloon 50 with an inflation source (not shown). Thus, the catheter 52 can assume any conventional form appropriate for percutaneously delivering the balloon 50 through a patient's vasculature (e.g., through the femoral artery and to the native valve to be repaired, such as across the aortic arch), such as a PEBAX® or other biocompatible plastic material catheter. The catheter 52 can optionally incorporate other features as desired (e.g., braided reinforced wall, a spring coil, guide wire lumen, multiple ports, etc.). Regardless, the catheter 52 extends between proximal and distal portions 54, 56 and establishes an inflation lumen (hidden in FIG. 2). The proximal portion 54 is connectable (e.g., via a manifold) to the inflation source, with the inflation lumen establishing a fluid connection between the inflation source and the balloon 50.

Figure 3A:
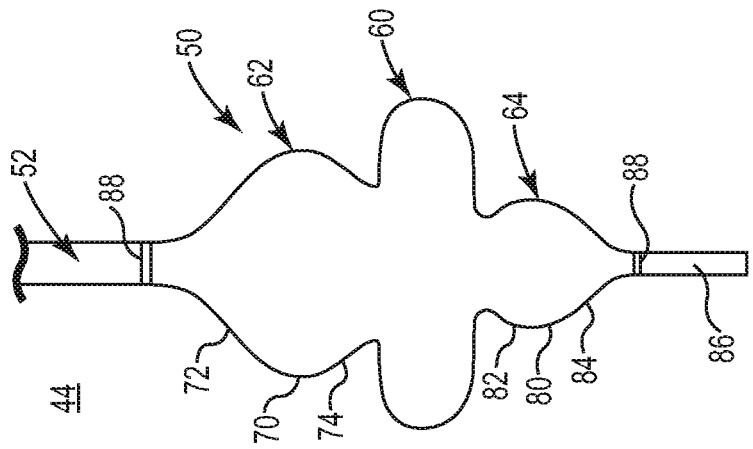
FIG. 3A is a simplified side view of a portion of a post-dilatation assembly component of the system of FIG. 2, including a balloon in a first profile of an inflated state.
Figure 3B:
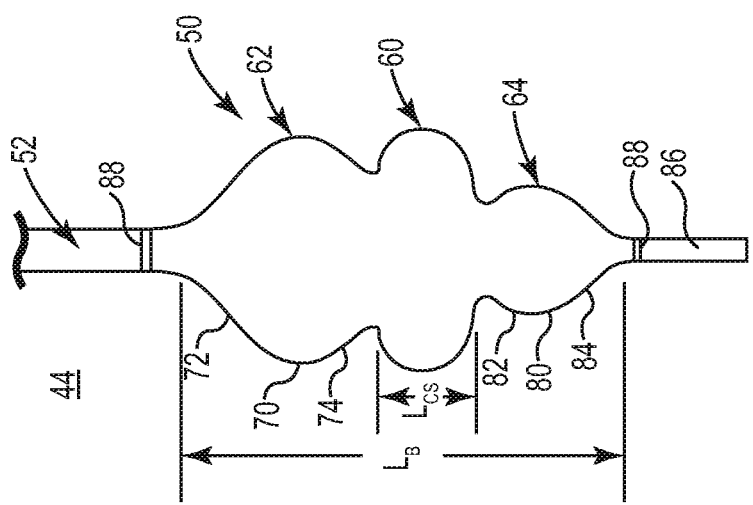
FIG. 3B is a simplified side view of the post-dilatation assembly of FIG. 3A, including the balloon in a second profile of the inflated state.

The balloon 50 is mounted to the distal portion 56 of the catheter 52, and is inflatable from the deflated state generally reflected in FIG. 2 to an inflated state configured to interface with an implanted stented prosthetic heart valve in a desired manner. For example, FIG. 3A illustrates the balloon 50 in a first profile of an inflated state, with the balloon 50 defining an intermediate segment 60, and opposing first and second end segments 62, 64. A compliance of the intermediate segment 60 is greater than that of the first end segment 62 and the second end segment 64. Stated otherwise, with continued inflation (e.g., increased internal pressure) of the balloon 50 from the first profile of the inflated state of FIG. 3A, the intermediate segment 60 will continue to expand in outer diameter at an elevated rate as compared to expansion of the end segment 62, 64, for example to a second profile of the inflated state shown in FIG. 3B. Thus, the intermediate segment 60 can be referred to as the compliant segment of the balloon 50. In some embodiments, the first and second end segments 62, 64 are essentially non-compliant, and will not radially expand beyond the predetermined shapes implicated by FIGS. 3A and 3B at expected inflation pressures (e.g., on the order of 0.5-8.0 ATM). That is to say, a shape and outer diameter of the end segments 62, 64 are essentially fixed upon inflation, regardless of inflation pressure, with the balloon 50 assuming the three-lobed shape as shown (with externally unconstrained expansion). While the intermediate segment 60 is radially expandable or compliant at least at the expected inflation pressures, the balloon 50 as a whole is substantially non-compliant in longitudinal length. A longitudinal working length $L_B$ of the balloon 50 remains substantially unchanged (e.g., no more than 5% change in longitudinal length) with continuous inflation of the balloon 50 (e.g., transitioning between the first and second profiles).

The intermediate compliant segment 60 is sized and shaped to interface with a selected region of the expanded, implanted prosthetic heart valve 20 (FIG. 1A), with this region being less than the longitudinal length $L_P$ (FIG. 1A) of the prosthesis 20. For example, in the inflated state of FIGS. 3A and 3B, the compliant segment 60 has a longitudinal length $L_{CS}$ that is less than the prosthesis length $L_P$. Thus, while the longitudinal working length $L_B$ of the balloon 50 may approximate (or exceed) the prosthesis length $L_P$, the compliant segment length $L_{CS}$ dictates that the compliant segment 60 will interface with or contact only a relatively small region or area of the implanted prosthetic heart valve 20 upon inflation and as described below. For example, the compliant segment 60 can be sized to interface with the constriction region 38 (FIG. 1A). The compliant segment 60 has, upon inflation, a generally obround shape in longitudinal cross-section, although other shapes (such as cylindrical) are also envisioned.

The first end segment 62 can have a predetermined shape in the inflated state selected to generally match an expected shape of a corresponding region of the deployed prosthetic heart valve 20 (FIG. 1A). For example, the inflated first end segment 62 can have the somewhat rounded shape as shown that otherwise mimics the expected shape of the outflow region 36 (FIG. 1A) of the deployed prosthetic heart valve 20. In this regard, a shape of the first end segment 62 in the inflated state can have or define a central section 70 and opposing, proximal and distal neck sections 72, 74. The central section 70 defines a maximum inflated outer diameter of the first end segment 62 (e.g., where the first end segment 62 is essentially non-compliant at expected inflation pressures, the maximum inflated outer diameter of the first end segment 62 is fixed) that can correspond with the expected maximum inner diameter of the outflow region 36. The proximal neck section 72 tapers in outer diameter (e.g., a fixed taper) from the central section 70 to a point of attachment with the catheter 52. The distal neck section 74 tapers in outer diameter (e.g., a fixed taper) from the central section 70 to the compliant segment 60. Other shapes (e.g., cylindrical) are also envisioned.

The second end segment 64 can also have a predetermined shape in the inflated state selected to generally correspond with an expected shape of a different region of the deployed prosthetic heart valve 20 (FIG. 1A). For example, the inflated second end segment 64 can have the somewhat elliptical shape as shown that otherwise mimics the expected shape of the inflow region 34 (FIG. 1A) of the deployed prosthesis 20. In this regard, a shape of the second end segment 64 in the inflated state can have or define a central section 80, and opposing, proximal and distal neck sections 82, 84. The central section 80 defines a maximum inflated outer diameter of the second end segment 64 (e.g., where the second end segment 64 is essentially non-compliant at expected inflation pressures, the maximum inflated outer diameter of the second end segment 64 is fixed) that can correspond with the expected maximum inner diameter of the inflow region 34. The proximal and distal neck sections 82, 84 can taper in outer diameter as shown, with this taper being fixed in some embodiments. Other shapes (e.g., cylindrical) are also envisioned.

The balloon 50 can be constructed in a variety of fashions. For example, in some embodiments, the balloon 50 is formed by blow-molding a uniaxially oriented polymer tube with a variable wall thickness. The variable wall thickness tube can be formed by post-necking an extruded tube. With this technique, the variable compliance attributes associated with the segments 60-64 as described above are achieved via the variable wall thickness. For example, a wall thickness of the balloon 50 along the compliant segment 60 is less than that of the end segments 62, 64, thereby rendering the compliant segment 60 more compliant than the end segments 62, 64. Other materials and/or manufacturing techniques are also envisioned. For example, an expansion limiting band or other inflation limiting structure can be applied (internally or externally) to one or both of the end segments 62, 64; the balloon segments 60-64 can be formed with different levels of cross-linking; different material(s) can be employed for the segments 60-64; etc. Regardless, the compliant segment 60 facilitates remodeling of a region of the implanted prosthetic heart valve 20 (FIG. 1A), whereas the less-compliant end segments 62, 64 serve to better locate, prevent migration, and support the compliant segment 60 during inflation.

The balloon 50 can be connected to the catheter 52 in various manners. For example, the balloon 50 can be an integrally formed component or extension of the catheter 52 tubing in accordance with the blow-molding techniques described above. Alternatively, the balloon 50 and the catheter 52 can be separately formed and subsequently assembled (e.g., adhesive bond; heat shrink; etc.). In some embodiments, a distal end 86 of the catheter 52 is provided distal the balloon 50 (i.e., the distal end 86 extends from the second end segment 64 of the balloon 50 in a direction opposite the compliant segment 60), for example by mounting the distal end 86 to the balloon 50 and/or via the integral molding techniques above. Regardless, one or more visual markers 88 (e.g., radiopaque band) can be applied along the catheter 52 at a location or locations immediately adjacent the balloon 50 to assist in properly locating the balloon 50 during use.

Figure 4:
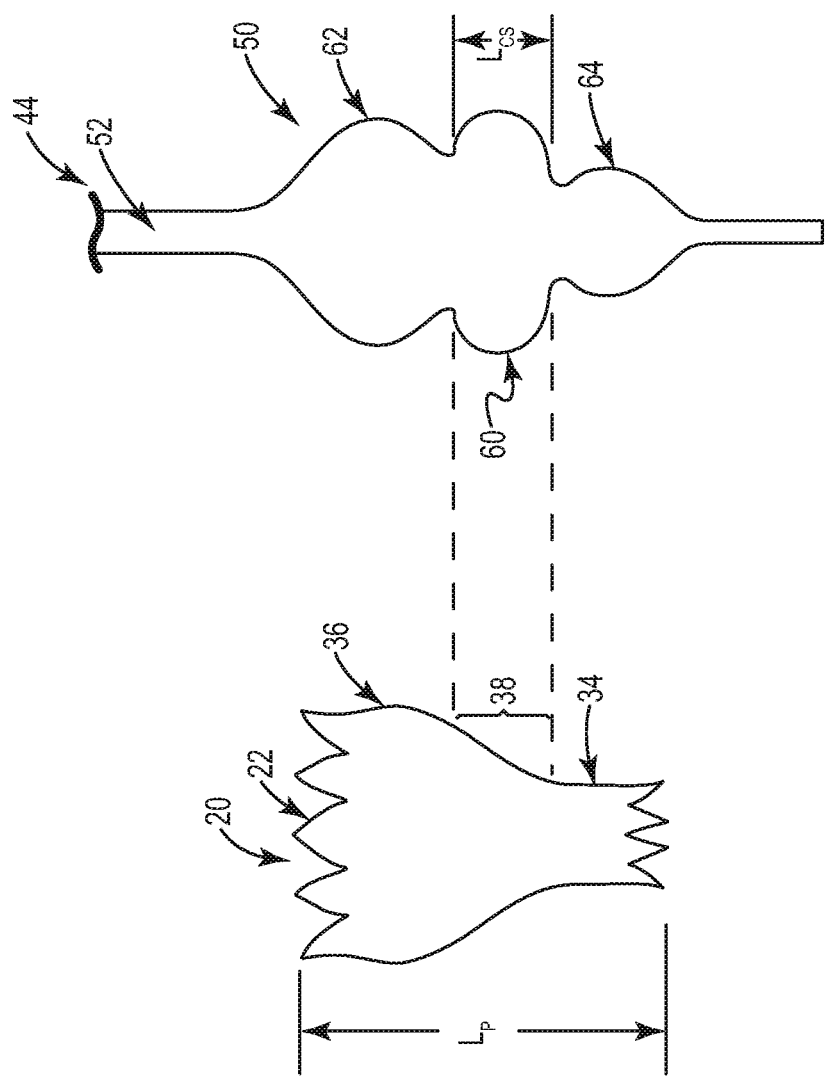
FIG. 4 is a simplified side view illustrating a comparison of the balloon of FIGS. 3A and 3B with the prosthetic heart valve of FIG. 1A.

As mentioned above, a size and shape of the balloon 50 is selected based upon the general size and shape of the prosthetic heart valve 20 (FIG. 1A) for which the balloon 50 will be used to remodel. By way of example, FIG. 4 provides a comparison of the balloon 50 with the prosthetic heart valve 20 in the normal, expanded arrangement. In the inflated state, the compliant segment length $L_{CS}$ is less than the prosthesis length $L_P$ (e.g., the compliant segment length $L_{CS}$ is no more than 75% of the prosthesis length $L_P$; in other embodiments, no more than 50%; and in yet other embodiments, no more than 40%). In one embodiment, the compliant segment length $L_{CS}$ is selected to approximate a longitudinal length of the constriction region 38. The first end segment 62 is generally sized in accordance with the outflow region 36, and the second end segment 64 is generally sized in accordance with the inflow region 34. When the balloon 50 is thus disposed within the implanted prosthetic heart valve 20 and inflated, the first end segment 62 may generally internally contact the stent frame 22 along the outflow region 36, and the second end segment 64 may generally internally contact the stent frame 22 along the inflow region 34. With the end segments 62, 64 so-located relative to the prosthetic heart valve 20, the compliant segment 60 contacts the stent frame 22 along the constriction region 38. With continued inflation of the balloon 50 from the first profile of FIG. 3A to the second profile of FIG. 3B, a radial expansive force applied to the constriction region 38 by the compliant segment 60 continuously increases. In contrast, the generally non-compliant nature of the first and second end segments 62, 64 is such that in transitioning of the balloon 50 from the first profile to the second profile, the contacted outflow and outflow regions 34, 36 do not further deflect with an increase in an inflation pressure or level of the balloon 50. Instead, the implanted prosthetic heart valve 20 is effectively "remodeled" primarily along the region (e.g., the constriction region 38) acted upon by the compliant segment 60.

Figure 5:
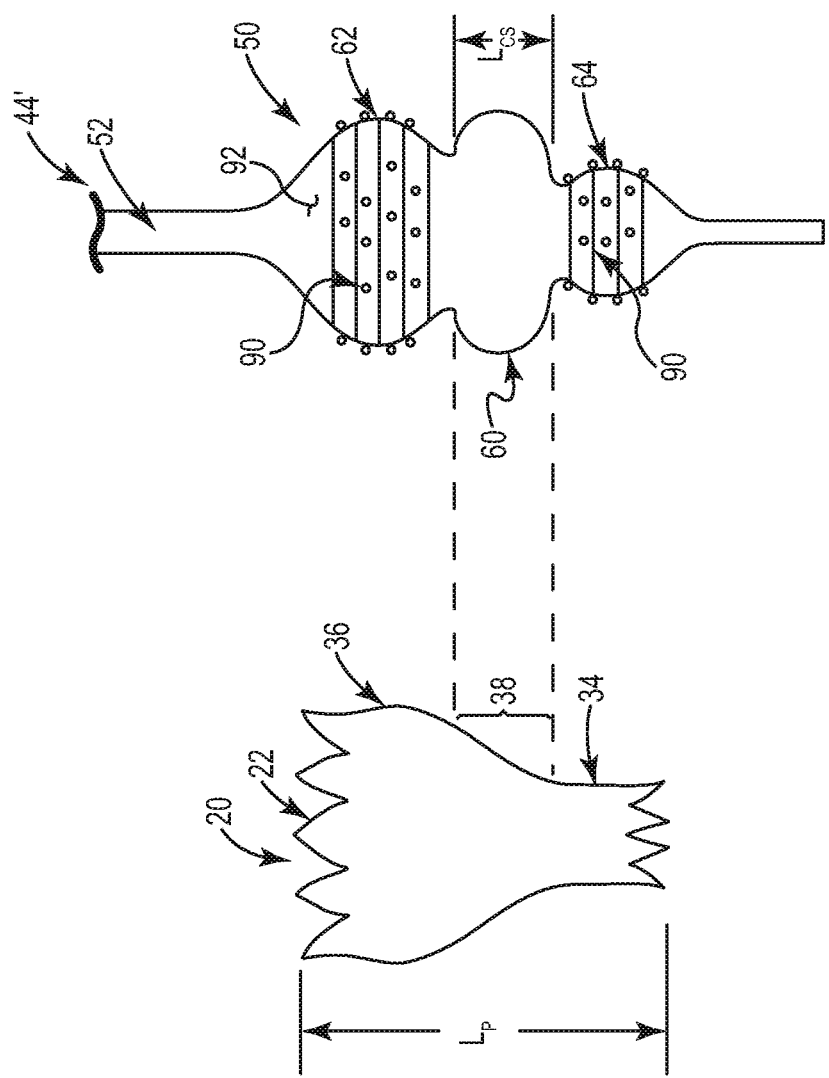
FIG. 5 is a simplified side view of a portion of another post-dilatation assembly in accordance with principles of the present disclosure and illustrating a comparison with the prosthetic heart valve of FIG. 1A.

The post-dilatation assembly 44 can incorporate additional features that promote positioning or anchoring of the compliant segment 60 relative to the region of the prosthesis 20 for which remodeling is desired (e.g., the constriction region 38). For example, FIG. 5 illustrates, in simplified form, a portion of an alternative post-dilatation assembly 44' that includes the balloon 50 and the catheter 52 as described above, as well as one or more prosthesis engagement features 90. The engagement features 90 are provided along an exterior surface 92 of the balloon 50 (e.g., an entire circumference of the exterior surface 92) at one or both of the first segment 62 and/or the second segment 64. The engagement features 90 can take various forms configured to frictionally interface with the stent frame 22, for example one or more of ridges, protrusions, surface roughness, high friction materials, etc. The engagement features 90 can be integrally formed by or into the balloon 50, or can be a structure apart from the balloon 50. Regardless, the engagement features 90 readily contract and expand with deflation/inflation of the balloon 50, and interact with the stent frame 22 to help anchor or position the compliant segment 60 relative to the desired remodeling region.

While the balloon 50 has been shown and described assuming the tri-lobed shape in the inflated state, other constructions are also acceptable. For example, one or both of the first and second end segments 62, 64 can be configured to have shapes differing from those illustrated. In yet other embodiments, the balloon 50 can include additional lobes in the inflated state. Conversely, one or both of the first and second end segments 62, 64 can be omitted.

Figure 6:
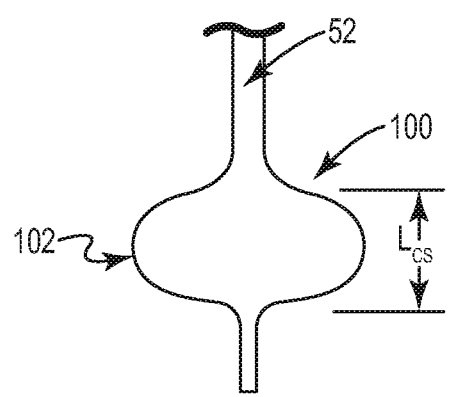
FIG. 6 is a simplified side view of another balloon useful with the post-dilatation assembly of FIG. 2.

For example, FIG. 6 illustrates, in simplified form, another balloon 100 in accordance with the present disclosure and useful with the post-dilatation assembly 44 (FIG. 2). The balloon 100 is assembled to the catheter 52 and consists of a compliant segment 102 akin to the compliant segment 60 (FIG. 3A) described above. The compliant segment 102 is formed to have a longitudinal length $L_{CS}$ (in the inflated state) that is less than the corresponding prosthesis length $L_P$ (FIG. 1A), and thus is configured to effectuate remodeling of only a desired region of an implanted prosthetic heart valve. In the inflated state of FIG. 6, the compliant segment 102 is disc-shaped (e.g., obround in longitudinal cross-section), and can be formed by expanding an extruded tube in the radial and axial directions, using applied temperature and pressure. With these and other techniques, the balloon 100 is integrally formed with the catheter 52, but alternatively can be separately manufactured and assembled thereto. The balloon 100 can be formed from various polymeric materials such as silicone, polyurethane, or other biocompatible thermoplastic elastomers such as C-Flex® available from Consolidated Polymer Technologies, Inc., of Clearwater, Fla. Though not shown, a visual marker(s) can be applied to the catheter 52 immediately adjacent the balloon 100.

Figure 7A:
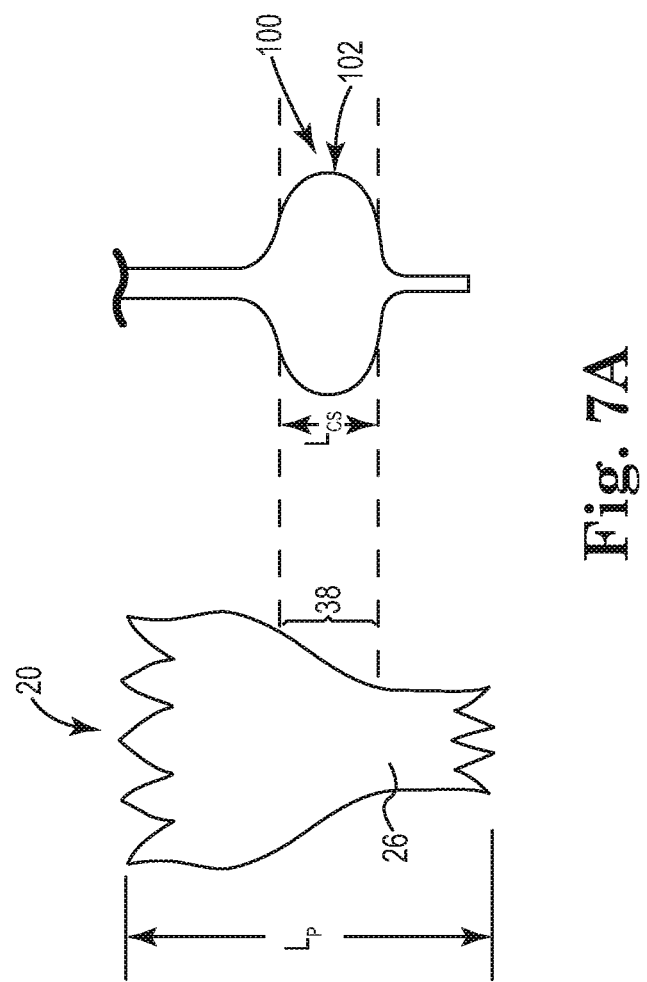
FIGS. 7A and 7B illustrate a comparison of the balloon of FIG. 6 with the prosthetic heart valve of FIG. 1A.
Figure 7B:
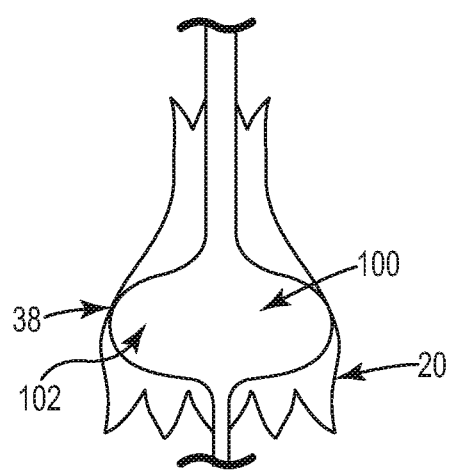

As compared to the balloon 50 (FIG. 3A), the balloon 100 does not include the first and second end segments 62, 64 (FIG. 3A). As shown in FIG. 7A, a length $L_{CS}$ of the compliant segment 102 is less than the prosthesis length $L_P$ and is selected to correspond generally with a length of a prosthesis region for which remodeling is desired, for example the constriction region 38. When the balloon 100 is disposed within the implanted prosthetic heart valve 20, the compliant segment 102 can be positioned such that when expanded, the compliant segment 102 is spaced from, and thus does not contact, the prosthetic heart valve leaflets 26 (referenced generally in FIG. 7A). With continued inflation, the compliant segment 102 will radially expand, but maintain a substantially fixed length. As a result, the constriction region 38 of the prosthetic heart valve 20 can be remodeled as shown in FIG. 7B with minimal or no expansive forces being placed upon the leaflets 26 by the balloon 100. Thus, the opportunity for possible damage to the leaflets 26 during remodeling is reduced.

Returning to FIG. 2, the delivery device 42 can assume various forms and generally includes the outer delivery sheath 46, an inner shaft assembly 110 (referenced generally), a handle 112, and an optional outer stability tube 114.

Representative configurations of the components 46, 110, 112, and 114 in accordance with some embodiments of delivery devices encompassed by the present disclosure are shown in greater detail in FIG. 8. In this regard, various features illustrated in FIG. 8 can be modified or replaced with differing structures and/or mechanisms. Thus, the present disclosure is in no way limited to the outer delivery sheath 46, the inner shaft assembly 110, the handle 112, or the stability tube 114 as shown and described below. In more general terms, then, delivery devices in accordance with principles of the present disclosure provide features capable of compressively retaining a self-expanding, stented prosthetic heart valve (e.g., the outer delivery sheath 46), along with one or more mechanisms capable of effectuating release or deployment of the heart valve prosthesis from the delivery device.

The outer delivery sheath 46 can include a capsule 120 and a shaft 122, and defines a lumen 124 (referenced generally) extending from a distal end 126 to a proximal end 128. The capsule 120 is attached to, and extends distally from, the shaft 122, and in some embodiments has a more stiffened construction (as compared to a stiffness of the shaft 122) that exhibits sufficient radial or circumferential rigidity to overtly resist the expected expansive forces of the stented prosthetic heart valve 20 (FIG. 1A) when compressed within the capsule 120. For example, the shaft 122 can be a polymer tube embedded with a metal braiding, whereas the capsule 120 includes a laser-cut metal tube that is optionally embedded within a polymer covering. Alternatively, the capsule 120 and the shaft 122 can have a more uniform construction (e.g., a continuous polymer tube). Regardless, the capsule 120 is constructed to compressively retain the stented prosthetic heart valve 20 at a predetermined diameter when loaded within the capsule 120, and the shaft 122 serves to connect the capsule 120 with the handle 112. The shaft 122 (as well as the capsule 120) is constructed to be sufficiently flexible for passage through a patient's vasculature, yet exhibits sufficient longitudinal rigidity to effectuate desired axial movement of the capsule 120. In other words, proximal retraction of the shaft 122 is directly transferred to the capsule 120 and causes a corresponding proximal retraction of the capsule 120. In other embodiments, the shaft 122 is further configured to transmit a rotational force or movement onto the capsule 120.

The inner shaft assembly 110 can have various constructions appropriate for supporting a stented prosthetic heart valve within the capsule 120. For example, the inner shaft assembly 110 can include a retention member 140, an intermediate tube 142, and a proximal tube 144. In general terms, the retention member 140 can be akin to a plunger, and incorporates features for retaining the stented prosthetic heart valve 20 (FIG. 1A) within the capsule 120 as described below. The intermediate tube 142 connects the retention member 140 to the proximal tube 144, with the proximal tube 144, in turn, coupling the inner shaft assembly 110 with the handle 112. The components 140-144 can combine to define a continuous lumen 146 (referenced generally) sized to slidably receive an auxiliary component such as a guide wire (not shown).

The retention member 140 can include a tip 150, a support tube 152, and a hub 154. The tip 150 forms or defines a nose cone having a distally tapering outer surface adapted to promote atraumatic contact with bodily tissue. The tip 150 can be fixed or slidable relative to the support tube 152. The support tube 152 extends proximally from the tip 150 and is configured to internally support a compressed, stented prosthetic heart valve generally disposed thereover, and has a length and outer diameter corresponding with dimensional attributes of the prosthetic heart valve. The hub 154 is attached to the support tube 152 opposite the tip 150 (e.g., adhesive bond) and provides a coupling structure 156 (referenced generally) configured to selectively capture a corresponding feature of the prosthetic heart valve. The coupling structure 156 can assume various forms, and is generally located along an intermediate portion of the inner shaft assembly 110. In some embodiments, the coupling structure 156 includes one or more fingers sized to be slidably received within corresponding apertures formed by the prosthetic heart valve stent frame 22 (FIG. 1A). For example, the stent frame 22 can form wire loops at a proximal end thereof that are releasably received over respective ones of the fingers when compressed within the capsule 120.

The intermediate tube 142 is formed of a flexible material (e.g., PEEK), and is sized to be slidably received within the delivery sheath 46, and in particular the shaft 122. The proximal tube 144 can include a leading portion 160 and a trailing portion 162. The leading portion 160 serves as a transition between intermediate and proximal tubes 142, 144, and thus can be a flexible tubing (e.g., PEEK) having a diameter slightly less than that of the intermediate tube 142. The trailing portion 162 has a more rigid construction, configured for robust assembly with the handle 112. For example, the trailing portion 162 can be a metal hypotube, although other constructions are also acceptable. In yet other embodiments, the intermediate and proximal tubes 142, 144 are integrally formed as a single, homogeneous tube or solid shaft.

The handle 112 generally includes a housing 170 and an actuator mechanism 172 (referenced generally). The housing 170 maintains the actuator mechanism 172, with the actuator mechanism 172 configured to facilitate sliding movement of the delivery sheath 46 relative to the inner shaft assembly 110, as well as relative to the optional stability tube 114 (where provided). The housing 170 can have any shape or size appropriate for convenient handling by a user. In one simplified construction, the actuator mechanism 172 includes a user interface or actuator 174 slidably retained by the housing 170 and coupled to a sheath connector body 176. The proximal end 128 of the delivery sheath 46 is coupled to the sheath connector body 176 (e.g., via an optional mounting boss 178 in some embodiments). The inner shaft assembly 110, and in particular the proximal tube 144, is slidably received within a passage 180 of the sheath connector body 176, and is rigidly coupled to the housing 170. Sliding of the actuator 174 relative to the housing 170 thus causes the delivery sheath 46 to move or slide relative to the inner shaft assembly 110, for example to effectuate deployment of a prosthesis from the inner shaft assembly 110. A cap 182 can be provided for attaching the optional outer stability tube 114 to the housing 170 (such that the delivery sheath 46 is slidable relative to the stability tube 114 with movement of the actuator 174), and can be configured to accommodate one or more optional port assemblies 184. In other embodiments, the stability tube 114 can be movably coupled to the housing 170 in a manner permitting selective sliding of the stability tube 114 relative to the delivery sheath 46 (and vice versa). In yet other embodiments, the stability tube 114 can be eliminated, such that the cap 182 is omitted as well. Similarly, the actuator mechanism 172 can assume a variety of other forms differing from those implicated by the illustration of FIG. 8.

Where provided, the stability tube 114 serves as a stability shaft for the delivery device 42, and defines a distal end 190, a proximal end 192, and a passageway 194 (referenced generally) extending between, and fluidly open at, the ends 190, 192. The passageway 194 is sized to coaxially receive the delivery sheath 46, and in particular the shaft 122, in a manner permitting sliding of the shaft 122 relative to the stability tube 114. Stated otherwise, an inner diameter of the stability tube 114 is slightly greater than an outer diameter of the shaft 122. The stability tube 114 has a length selected to extend over a significant portion (e.g., at least a majority, and in other embodiments, at least 80%) of a length of the shaft 122 in distal extension from the handle 112. Further, the stability tube 114 exhibits sufficient radial flexibility to accommodate passage through a patient's vasculature (e.g., the femoral artery, aortic arch, etc.). In yet other embodiments, the stability tube 114 is omitted.

The system 40 (FIG. 2) can be utilized to restore (e.g., replace) a defective heart valve of a patient. Initially, the delivery device 42 is loaded with the stented prosthetic heart valve 20 as illustrated, in simplified form, in FIGS. 9A and 9B. For ease of illustration, the valve structure 24 (FIGS. 1A and 1B) is omitted, and only the stent frame 22 is shown. The prosthetic heart valve 20 is disposed over the inner shaft assembly 110, with the proximal region (e.g., outflow region) 36 being crimped into engagement with the coupling structure 156. The capsule 120 is slidably disposed over the prosthetic heart valve 20, compressively retaining the prosthesis 20 about the inner shaft assembly 110. In the loaded state of FIGS. 9A and 9B, then, the prosthetic heart valve 20 is compressed retained in the compressive arrangement by the delivery device 42.

Figure 10:
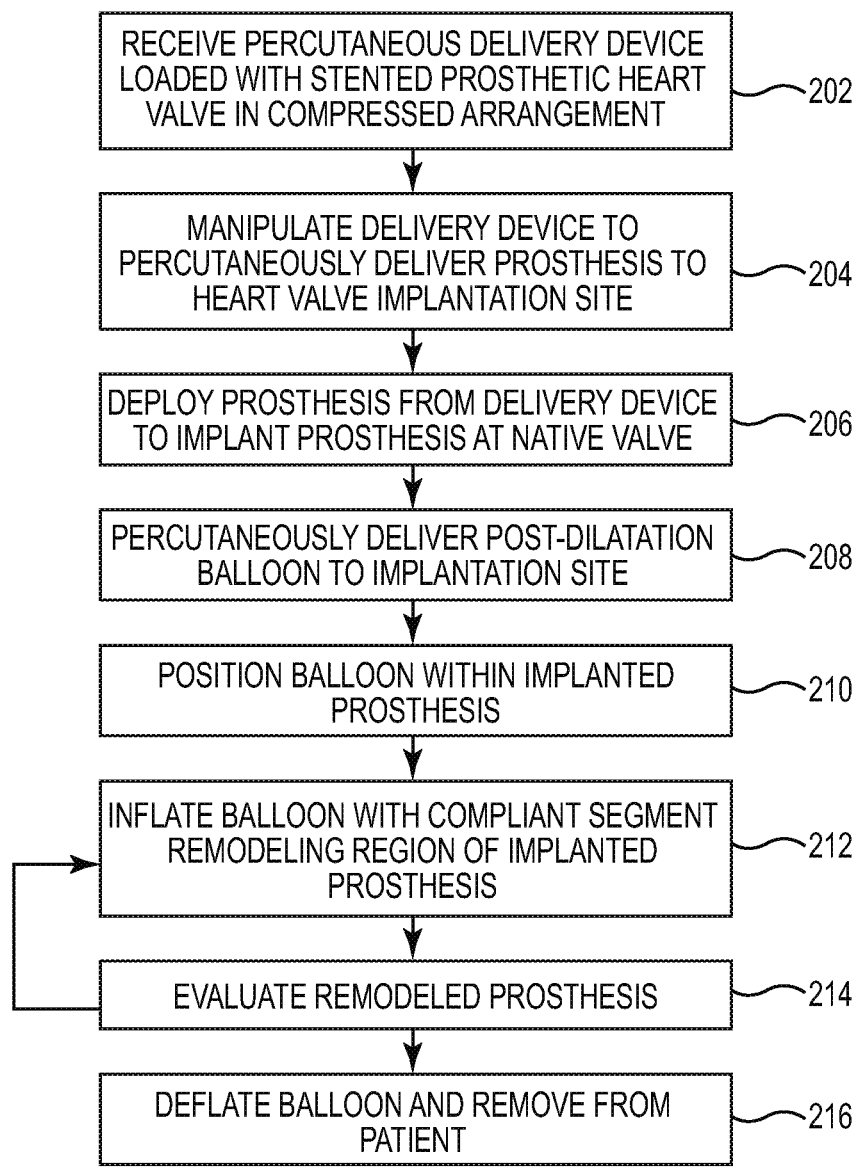
FIG. 10 is a flow diagram of a method for repairing a defective heart valve in accordance with principles of the present disclosure.
Figure 11A:
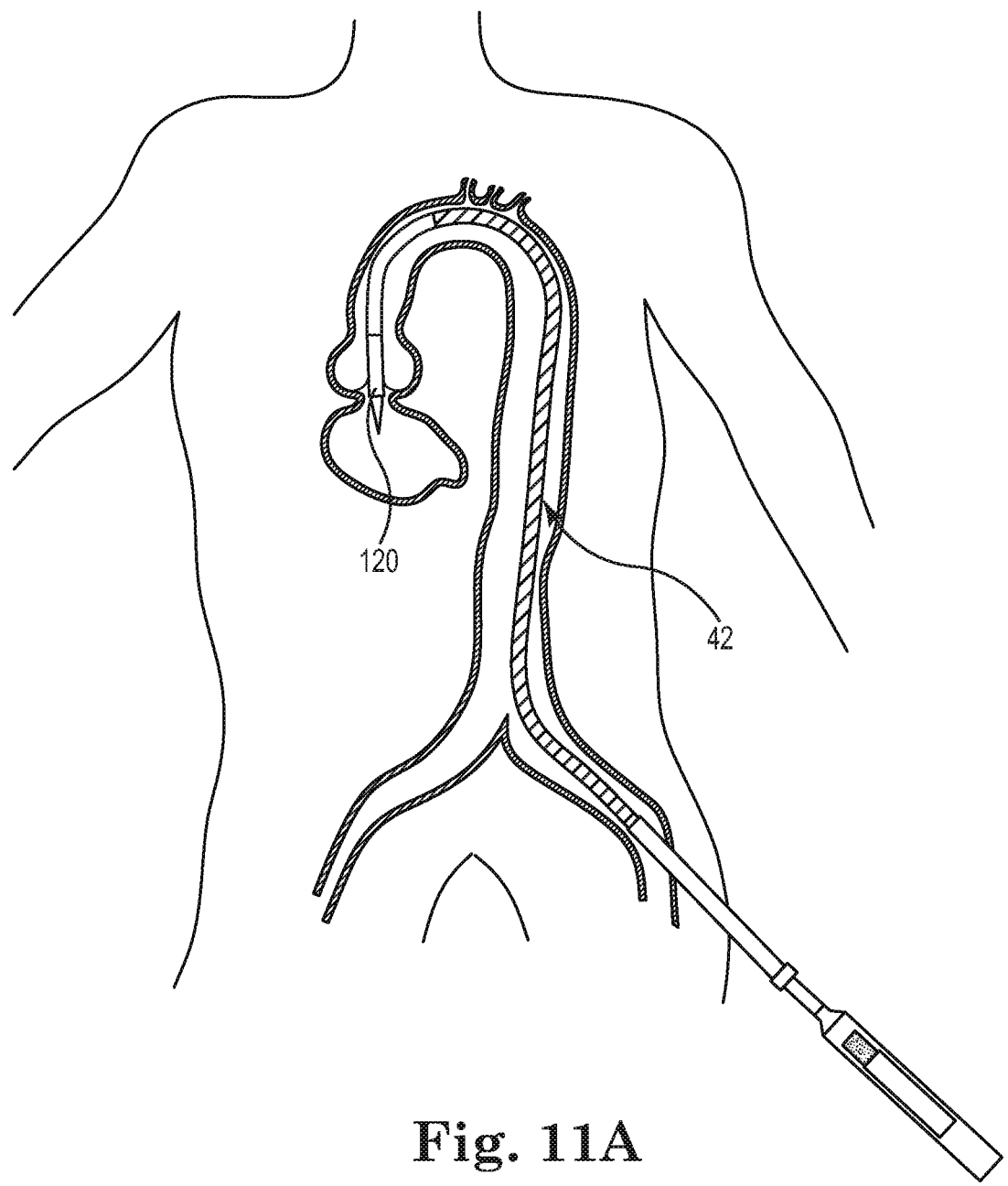
FIGS. 11A and 11B are simplified anatomical views of a delivery device percutaneously implanting a stented heart valve.
Figure 11B:
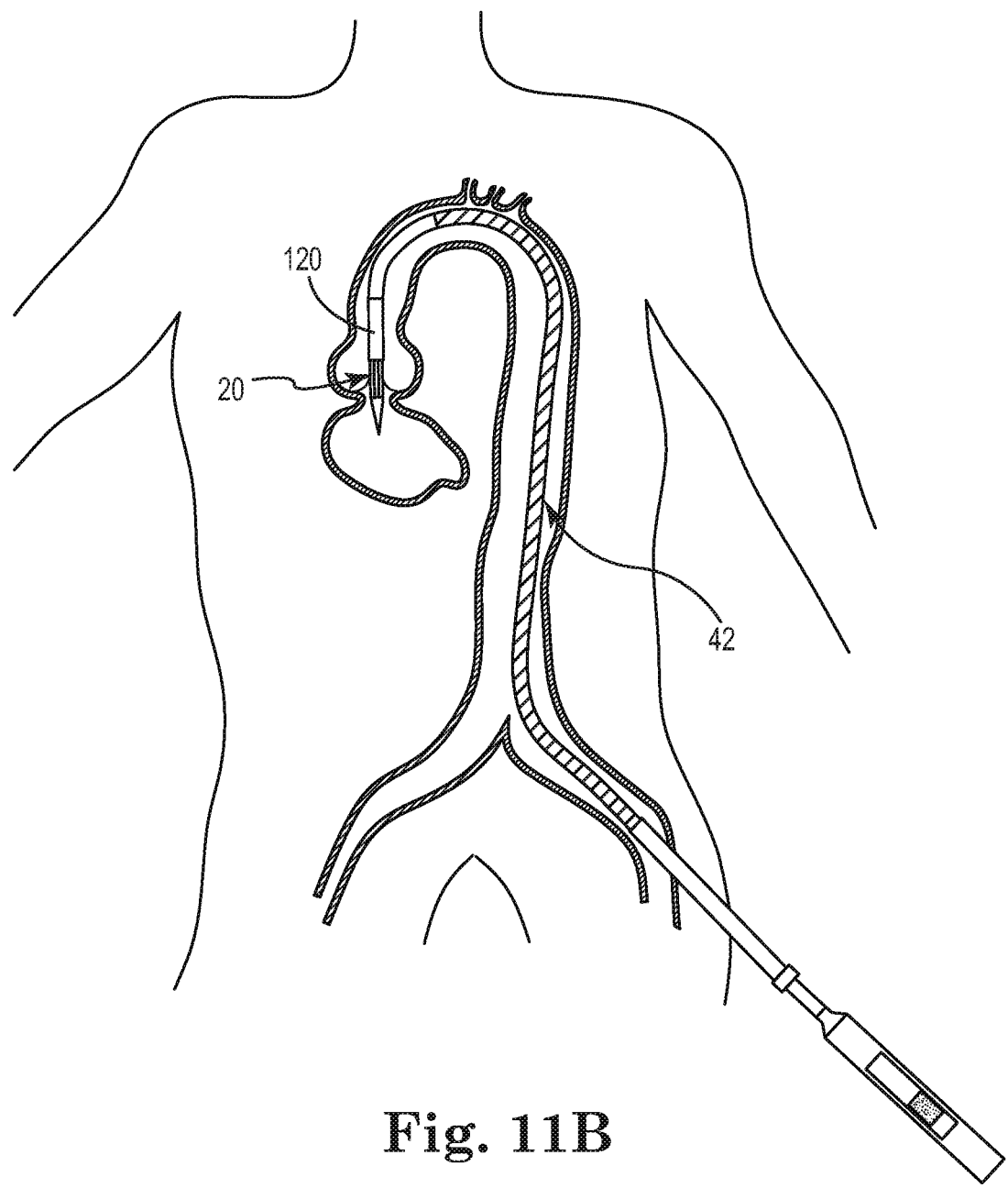

With additional reference to the flow diagram of FIG. 10, one method 200 for restoring (e.g., replacing) a defective heart valve begins at 202 in which a clinician receives the prosthetic heart valve 20/delivery device 42 in the loaded state. The delivery device 42 is then, at 204, manipulated to percutaneously deliver the prosthetic heart valve 20 (in the compressed arrangement) to a defective heart valve implantation site. For example, the delivery device 42 is manipulated to advance the prosthetic heart valve 20 toward the implantation site in a retrograde manner through a cut-down to the femoral artery, into the patient's descending aorta, over the aortic arch, through the ascending aorta, and approximating mid-way across the defective aortic valve for an aortic valve replacement procedure. This positioning is generally reflected in FIG. 11A. The prosthetic heart valve 20 is then deployed from the delivery device 42 at 206. As a point of reference, prior to full deployment of the prosthetic heart valve 20, a partial deployment and evaluation procedure can be performed in which the prosthetic heart valve 20 is partially deployed from the delivery device 42 and a position of the so-deployed region relative to the implantation site evaluated. Regardless, and as generally reflected in FIG. 11B, deployment of the prosthetic heart valve 20 generally entails retraction of the capsule 120 from the prosthetic heart valve 20 as described above. Once released from the delivery device 42, the prosthetic heart valve 20 self-expands from the compressed arrangement toward a natural arrangement, thereby self-implanting to the implantation site.

Figure 12A:
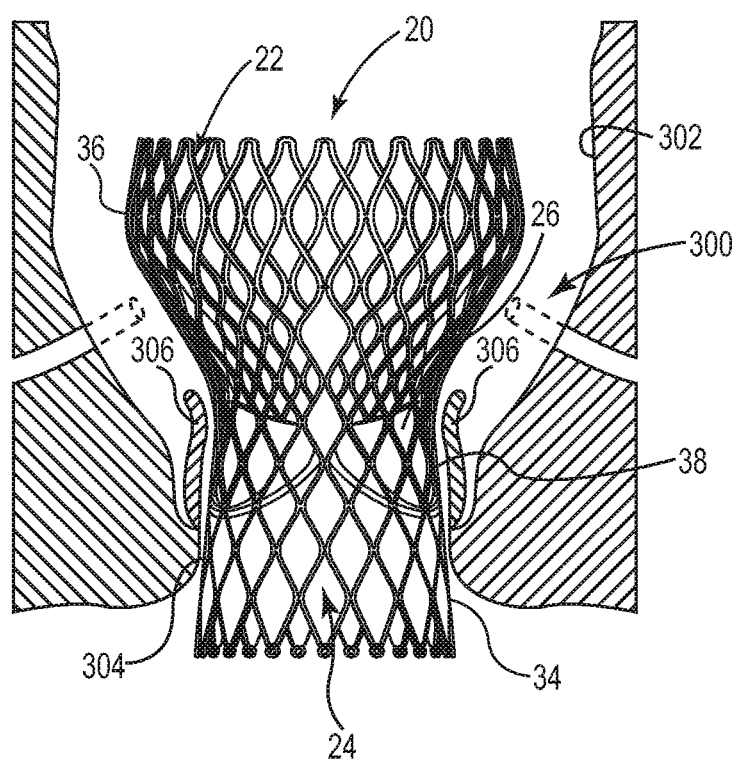
FIGS. 12A-12C illustrate various steps of the method of FIG. 10.

One representation of the implanted prosthetic heart valve 20 (prior to remodeling) relative to a representative native aortic heart valve anatomy 300 is shown in FIG. 12A. In the initial implanted state, the stent frame 22 has self-expanded, with the outflow region 36 expanding toward, and aligning the prosthesis 20 within, an ascending aorta 302. The inflow region 34 has expanded within the annulus 304 of the valve anatomy 300. The deployed configuration of the constriction region 38 holds the valve structure 24 in a supra-annular position, above the basal plane and/or above the diseased native leaflets, away from the heart walls and coronary ostia. Further, the implanted prosthesis traps native leaflets 306 against the valve annulus 304, thereby retaining the native valve 300 in an open state.

Figure 12B:
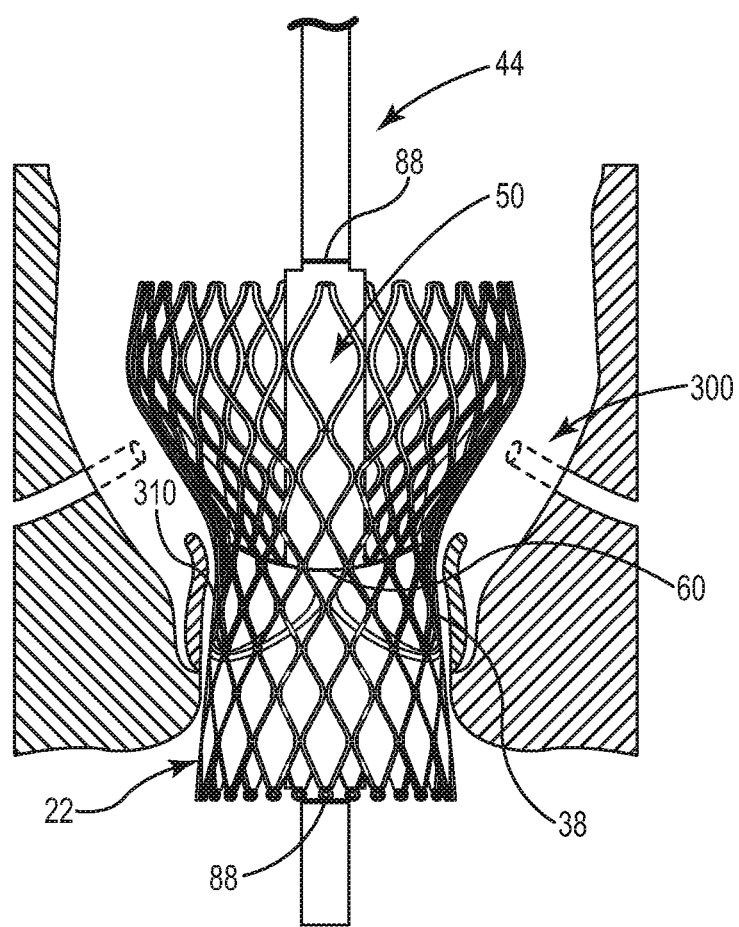

With cross-reference between FIGS. 10 and 12B, at 208, the balloon 50 (or the balloon 100 (FIG. 6)) is percutaneously delivered to the implantation site 300. In this regard, delivery of the balloon 50 can include removing the delivery device 42 (FIG. 11A) from the patient, and then manipulating the post-dilatation assembly 44 through the same vasculature path to generally locate the balloon 50 at the implantation site 300. In other embodiments, the delivery device 42 can be constructed such that the balloon 50 is delivered through an interior lumen of the delivery device 42, and located distally beyond the tip 150 (FIG. 8). Regardless, at 210, the balloon 50 is axially disposed within the implanted prosthetic heart valve 20 as shown in FIG. 12B. In this regard, the balloon 50 is arranged such that the compliant segment 60 is axially aligned with a region 310 of the prosthetic heart valve 20 for which remodeling is desired. The selected remodeling region 310 can be the constriction region 38 of the prosthetic heart valve 20, between the leaflets 26 and the outflow end 32. Alternatively, any other region of interest to the clinician can be selected. With methodologies in which the constriction region 38 serves as the remodeling region 310, the marker (s) 88 provided with or adjacent the balloon 50 can be aligned with a corresponding end of the stent frame 22 via imaging technology so as to more accurately locate the compliant segment 60 relative to the remodeling region 310.

Figure 12C:
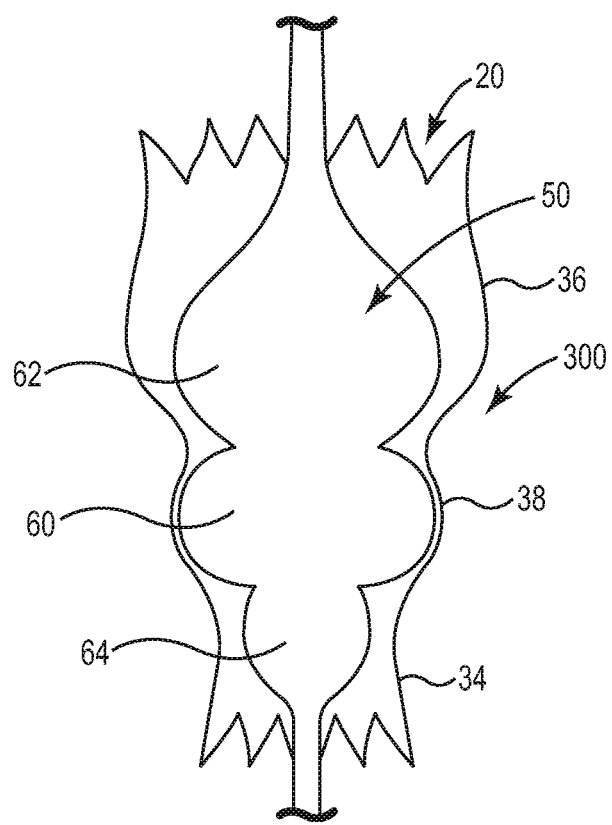

With reference to FIGS. 10 and 12C, at 212, the balloon 50 is inflated. The first end segment 62 expands to a predetermined outer shape and diameter, as does the second end segment 64. In instances where the implanted prosthetic heart valve 20 has fully expanded, the end segments 62, 64 may or may not slightly contact corresponding regions of the implanted prosthetic heart valve 20. Conversely, where self-expansion was less than complete, the first end segment 62 and/or the second end segment 64 may more overtly engage the corresponding region of the implanted prosthetic heart valve 20 and with inflation, cause more complete expansion thereof. Regardless, the correspondence in shape of the inflated end segments 62, 64 with that of the outflow and inflow regions 36, 34, respectively, guides the compliant segment 60 into better alignment with the constriction region 38 (or other region to be remodeled). In other embodiments, optional engagement features (e.g., the engagement features 90 in FIG. 5) achieve a more positive interface between the segments 62, 64 and the implanted prosthesis 20, thereby enhancing positioning and anchoring of the compliant segment 60 relative to the remodeling region 310. With continued inflation, the compliant segment 60 contacts the remodeling region 310, and forces the stent frame 22 to deform in general correspondence with the shape of the inflated compliant segment 60. At 214, the so-remodeled prosthetic heart valve 20 can again be evaluated relative to the native anatomy of the implant site 300. If necessary, the balloon 50 can be subjected to an elevated inflation pressure, causing the compliant segment 60 to further radially expand to a second profile. As previously described, however, the first and second end segments 62, 64 experience minimal, if any, radial expansion at the elevated inflation pressure, with the expansive forces of the balloon 50 thus being focused upon the remodeling region 310. Thus, the end segments 62, 64 can be located adjacent areas of concern such as the conduction system (e.g., AV node, left bundle branch, paraspecific fibers of mahaim), anterior mitral leaflet, etc., but will not contact (or only minimally contact) the areas of concern with inflation of the balloon 50.

The steps of evaluating the shape of the remodeled prosthetic heart valve 20 and increasing the inflation pressure (and thus the outer diameter or exerted radially outward expansive force of the compliant segment 60) is repeated until the clinician is satisfied with the shape of the remodeled implanted prosthetic heart valve 20. Once the clinician is satisfied, the balloon 50 is deflated and removed from the patient at 216. The remodeled shape as effectuated by the balloon 50 is retained by the prosthetic heart valve 20.

The balloon 100 (FIG. 6) can be utilized in a manner highly similar to that described above with respect to the balloon 50. As previously mentioned, by forming the balloon 100 to include only the compliant segment 102 (FIG. 6), the clinician can more easily focus the expansive forces of the balloon 100 onto the remodeling region 310, and can thus avoid contacting or otherwise exerting an overt force onto the prosthetic leaflets 26 or other areas of concern noted above.

The systems, devices, and methods of the present disclosure provide a marked improvement over previous designs. The post-dilatation balloon and use thereof facilitates remodeling of an implanted transcatheter prosthetic heart valve with a self-expanding stent frame. The systems, devices, and methods of the present disclosure are minimally invasive, yet provide techniques for ensuring the implanted prosthetic heart valve more closely matches the native anatomy and minimizes the risks for paravalvular leaks. In some embodiments, the post-dilatation balloon provides custom shape and compliance features that avoid damaging the prosthetic leaflets when effectuating remodeling of the implanted prosthesis.

Although the present disclosure has been described with reference to preferred embodiments, workers skilled in the art will recognize that changes can be made in form and detail without departing from the spirit and scope of the present disclosure. For example, the post-dilatation balloon assembly can be used with balloon-expandable type stented prosthetic heart valve delivery devices. With these alternative embodiments, a first, deployment balloon is employed to generally deploy the prosthesis from the delivery device, and a second, remodeling balloon in accordance with the present disclosure is utilized to effectuate desired remodeling.

What is claimed is:

1. A post-dilatation assembly for remodeling an implanted stented prosthetic heart valve, the assembly comprising:
   a catheter defining an inflation lumen;
   a balloon carried by the catheter and in fluid communication with the inflation lumen;
   wherein the balloon defines an intermediate segment, a first end segment proximal the intermediate segment, and a second end segment distal the intermediate segment;
   and further wherein the first and second end segments are less compliant than the intermediate segment;
   and even further wherein in an inflated state, the first end segment tapers in outer diameter from a maximum diameter to a transition point with the intermediate segment.

2. The assembly of claim 1, wherein in the inflated state, the second end segment tapers in outer diameter from a maximum diameter to a transition point with the intermediate segment.

3. The assembly of claim 2, wherein in the inflated state, the maximum diameter of the first end segment is greater than the maximum diameter of the second end segment.

4. The assembly of claim 1, wherein a predetermined shape of the first end segment upon inflation differs from a predetermined shape of the second end segment upon inflation.

5. The assembly of claim 1, wherein the first end segment in the inflated state defines a central section and opposing, proximal and distal neck sections, and further wherein the distal neck section has a fixed taper in outer diameter from the central section to the intermediate segment.

6. The assembly of claim 1, wherein the balloon is configured such that at inflation pressures on the order of 0.5-8.0 ATM, the intermediate segment defines an obround shape in longitudinal cross-section.

7. The assembly of claim 1, wherein the balloon is configured such that at inflation pressures on the order of 0.5-8.0 ATM, the second end segment defines an elliptical shape.

8. The assembly of claim 1, wherein the balloon is configured such that at inflation pressures on the order of 0.5-8.0 ATM, a maximum outer diameter of the intermediate segment continuously expands and the first and second end segments do not expand beyond a predetermined shape.

9. The assembly of claim 8, wherein the balloon is substantially non-compliant in longitudinal length at inflation pressures on the order of 0.5-8.0 ATM.

10. The assembly of claim 1, wherein the catheter and the balloon are integrally formed as a continuous tube.

* * * * *